United States Patent
Aspelund et al.

(10) Patent No.: US 10,881,374 B2
(45) Date of Patent: Jan. 5, 2021

(54) MAMMOGRAPHY IMAGING ARRANGEMENT FOR TOMOSYNTHESIS

(71) Applicant: PLANMED OY, Helsinki (FI)

(72) Inventors: Leo Aspelund, Helsinki (FI); Tapio Laukkanen, Espoo (FI); Kustaa Nyholm, Siuntio (FI); Jaakko Lahelma, Helsinki (FI)

(73) Assignee: Planmeca OY, Helsinki (FI)

( * ) Notice: Subject to any disclaimer, the term of this patent is extended or adjusted under 35 U.S.C. 154(b) by 492 days.

(21) Appl. No.: 15/039,760

(22) PCT Filed: Dec. 1, 2014

(86) PCT No.: PCT/FI2014/050936
§ 371 (c)(1),
(2) Date: May 26, 2016

(87) PCT Pub. No.: WO2015/079120
PCT Pub. Date: Jun. 4, 2015

(65) Prior Publication Data
US 2017/0000451 A1    Jan. 5, 2017

(30) Foreign Application Priority Data
Nov. 29, 2013    (FI) ...................................... 20130359

(51) Int. Cl.
*A61B 6/00* (2006.01)
*A61B 6/02* (2006.01)

(52) U.S. Cl.
CPC .............. *A61B 6/583* (2013.01); *A61B 6/025* (2013.01); *A61B 6/502* (2013.01); *A61B 6/5258* (2013.01); *A61B 6/582* (2013.01)

(58) Field of Classification Search
CPC ....... A61B 6/502; A61B 6/0414; A61B 6/583; A61B 6/025; A61B 6/5258; A61B 6/582
See application file for complete search history.

(56) References Cited

U.S. PATENT DOCUMENTS

| | | | | |
|---|---|---|---|---|
| 4,943,986 A | * | 7/1990 | Barbarisi | A61B 6/502 378/208 |
| 7,699,523 B2 | * | 4/2010 | Shinden | A61B 6/0414 378/208 |

(Continued)

FOREIGN PATENT DOCUMENTS

| | | |
|---|---|---|
| WO | 2006058160 A2 | 6/2006 |
| WO | 2010061062 A1 | 11/2009 |

(Continued)

OTHER PUBLICATIONS

Translation of JP 2012-115380 published Jun. 21, 2012.*

*Primary Examiner* — Chih-Cheng Kao
(74) *Attorney, Agent, or Firm* — Fay Sharpe LLP

(57) ABSTRACT

The invention relates to a tomosynthesis process in the context of mammography, in which several individual images of a breast are taken at different projection angles and in which of information thus acquired, tomographic images are synthesized with the help of an applicable image processing software. The mutual geometry of the imaging means of the imaging apparatus when taking these individual images is determined according to the invention by arranging in the imaging apparatus a calibration structure (20), which includes balls (21) or other small objects absorbing X-radiation which are such placed that their projections will become imaged on said individual images.

5 Claims, 8 Drawing Sheets

(56) References Cited

U.S. PATENT DOCUMENTS

Figure 1:
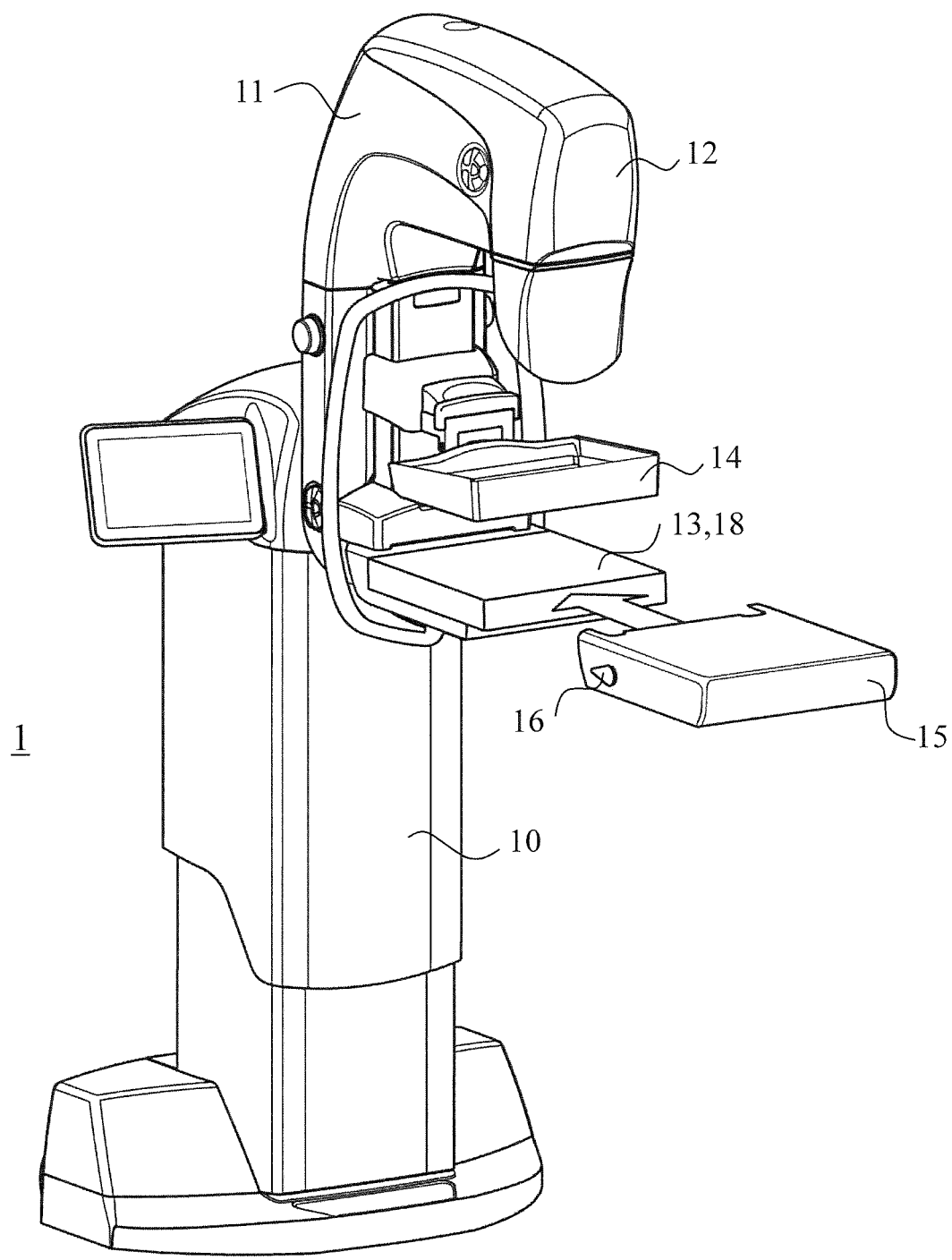

| | | | |
|---|---|---|---|
| 7,778,392 B1* | 8/2010 | Berman | A61B 6/032 |
| | | | 378/210 |
| 2001/0034482 A1 | 10/2001 | Webber et al. | |
| 2002/0131559 A1 | 9/2002 | Launay et al. | |
| 2005/0008117 A1* | 1/2005 | Livingston | A61B 6/0414 |
| | | | 378/37 |
| 2005/0113681 A1* | 5/2005 | DeFreitas | A61B 6/502 |
| | | | 600/426 |
| 2005/0113682 A1 | 5/2005 | Webber | |
| 2007/0122020 A1 | 5/2007 | Claus et al. | |
| 2008/0186311 A1 | 8/2008 | Claus | |
| 2009/0022264 A1* | 1/2009 | Zhou | A61B 6/025 |
| | | | 378/5 |
| 2009/0268865 A1* | 10/2009 | Ren | A61B 6/0414 |
| | | | 378/37 |
| 2010/0091940 A1* | 4/2010 | Ludwig | A61B 6/025 |
| | | | 378/22 |
| 2012/0051500 A1 | 3/2012 | Johansson | |
| 2012/0163537 A1* | 6/2012 | Iwakiri | A61B 6/4283 |
| | | | 378/62 |
| 2014/0119500 A1 | 5/2014 | Akahori | |

FOREIGN PATENT DOCUMENTS

| | | |
|---|---|---|
| WO | 2010061003 A1 | 6/2010 |
| WO | 2013005833 A1 | 1/2013 |
| WO | 2013035023 A1 | 3/2013 |

* cited by examiner

MAMMOGRAPHY IMAGING ARRANGEMENT FOR TOMOSYNTHESIS

FIELD OF INVENTION

The present invention relates to a tomosynthesis process in the context of mammography, in which process several images of a breast are taken at different projection angles, such as in the range of ±15 degrees from the vertical, and in which one can synthesize tomographic images from the image information thus acquired with the help of applicable image processing software.

DESCRIPTION OF PRIOR ART

Breast cancer is the most common type of cancer in women. According to studies, about one in every ten women contracts breast cancer at some point in their lives. When breast cancer is detected on the basis of symptoms, the illness has often already developed into a stage where the prognosis for recovery is relatively poor. Some of the cases are detected in screening programs arranged in many countries for women over the age of 40. Screening often reveals a cancer at a very early stage, whereby its treatment can be started in time and recovery is thus more likely.

Mammography is a widely used method in breast cancer screening both as a clinical investigation method and in follow-up diagnosis. Mammography is an X-ray imaging method wherein an apparatus specifically designed for this purpose is used. In screening studies, mammography has been reported having sensitivity of 90-93% and specificity of 90-97%. This indicates that screening studies are useful and that early detection of breast cancer by screening can save human lives. It has been established that mammography reduces breast cancer mortality by 35 percent among women over 50 and by 25-35 percent among women in the age group of 40-50.

Mammography images are examined to detect various anomalies in the breast, such as calcifications i.e. small deposits of calcium in the soft breast tissue. A calcification generally cannot be detected by feeling the breast, but it is visible in the X-ray image. Large calcifications are not generally associated with cancer, but clusters of small calcium deposits, i.e. so-called microcalcifications, are an indication of extra breast cell activity which may be associated with breast cancer. Other features to be detected by mammography include cysts and fibroadenomas which, however, are not generally associated with cancer.

In conventional screening mammography, a breast gland is typically compressed between two compression plates and exposed to radiation at least twice, from above and from an oblique direction. If necessary, an additional third image is taken squarely from the side. As tissue layers lie on top of each other in the direction of the X-ray beam in such imaging, these irradiations produce two-dimensional images in which strongly absorbing structures may hinder the detection of structures lying beneath them.

Continuous development of mammography has led to novel types of mammography methods and devices with the help of which a breast can be examined also by means other than two-dimensional images. When a breast is imaged at several projections angles, a 3D distribution of the breast can be created by using an applicable reconstruction algorithm. In tomosynthesis, several images orientating in parallel with the surface of the X-ray detector and showing different layers of the breast are typically generated from a group of individual radiographs. It may be possible to detect from those images such tissue structures which lie on top of each other and thus cannot be detected from an individual radiograph.

A typical modern digital mammography apparatus comprises a frame part and a C-arm or a corresponding structure rotatably connected to the frame part. At a first end of the C-arm is arranged an x-ray source and, at a second end, a radiation detector. A term imaging means is often used for these devices, substantially in the region between said X-ray source and detector, typically at a close proximity to the detector, compression plates are arranged which are designed for positioning the breast as compressed for the duration of an exposure.

In prior art, in the context of 3D mammography apparatuses, various ways to image the breast at a number of different projection angles have been used or suggested. These include continuously turning the X-ray source with a constant or an alternating speed along a curved path about the breast, turning the X-ray source step-by-step between exposures during which the X-ray source remains still, and using multiple stationary X-ray sources. Depending on the detector and the construction of the apparatus, the detector may be kept stationary, moved linearly and/or tilted and/or moved such that it will remain at the same position with respect to the X-ray beam in each projection.

The X-ray source is typically a relatively heavy component for a C-arm of a mammography apparatus to support. In the case of the step-by-step movement of the X-ray source, the imaging apparatus should have reached a vibration-free status prior to each exposure. Then, the structures of the mammography apparatus should be optimized in view of the number of accelerations, decelerations and stops (stabilization times) included in the multi-phase imaging procedure. The overall time needed for an imaging procedure like this tends to become quite long.

On the other hand, in the case of the continuous movement of the X-ray source, remarkably short exposure times, such as less than 50 ms, must be used in order to avoid creating movement artefacts. This in turn calls for using a powerful enough radiation source, which means using an even heavier X-ray source then those typically used in prior art 2D mammography apparatuses and, consequently, other constructions of the imaging apparatus must be designed in view of this greater mass as well.

Arranging several X-ray sources in a mammography apparatus calls for, again, a completely new type of design for a mammography apparatus. It is a challenge when such a mechanical structure is used to be able to come up with a construction which would also be practical in view of using the apparatus for conventional 2D screening mammography.

One novel solution is to implement imaging such that the movement of the X-ray source is implemented constant but, to avoid movement artefacts, also e.g. the compression plates compressing the breast and optionally simultaneously the detector are moved during short exposure periods such that they follow the movement of the X-ray source. Men, no movement artefacts are created during an exposure and the compression plates can always be returned to their starting position before the next irradiation pulse. Such technology has been described, inter alia, in a WO publication 2010/061062.

In mammography, findings extremely snail of their size are searched for from the image information. From the viewpoint of processing of image information in connection with tomosynthesis imaging, it would be preferable to know the imaging geometry prevailed in connection with the imaging as precisely as possible. When certain gaps and tolerances typically relate to mechanical structures, knowledge in theory of the dimensions and paths of the imaging apparatus and its components does not necessarily enable achieving a required precision. Calibrating the mammography imaging arrangement prior to the imaging event does not necessarily create information which will correspond to the actual imaging geometry realized during the imaging, for the part of all images taken in the process. While the comments of the imaging apparatus more during the imaging process they are vulnerable to external forces, such as gravity, and even the patient positioned for imaging may cause when leaning or supporting herself on the imaging apparatus during imaging, bending in the apparatus structures or movement of them diverging from the calculated.

Generally speaking, it is not necessarily that straightforward to modify a mammography apparatus designed for conventional screening to also be applicable for tomosynthesis imaging and, correspondingly, it is not necessarily that straightforward to make a mammography apparatus designed for tomosynthesis imaging also applicable for conventional screening.

SUMMARY OF INVENTION

The object of the present invention and its preferable embodiments is to enable tomosynthesis of individual 2D images taken by a mammography apparatus such that the mutual geometry of the imaging means of the imaging apparatus is determined, separately, for each individual image when taking the image. The object is thus a solution thanks to which the actual imaging device does not necessarily have to be extremely precise of its mechanical structures and movements as the imaging geometry can always be calculated based on calibration information projected into each individual 2D image. Preferable embodiments of the invention include solutions which can enable a relatively simple updating of conventional mammography apparatuses to be applicable also for tomosynthesis imaging.

The object of the invention is reached by the solutions of the independent claims attached hereto. Some preferable embodiments of the invention are presented in the attached dependent claims.

The invention and its preferable embodiments enable generating precise tomosynthesis images irrespective of the mechanical properties of the imaging apparatus. The existing imaging devices designed for conventional mammography imaging, including devices which in itself do not necessarily include means to produce precise information on the location or movements of the imaging means during an imaging process can be used for tomosynthesis. Particular preferable embodiments of the invention enable modification of at least some conventional prior-art mammography apparatuses to be applicable also for tomosynthesis imaging by arranging the apparatus with only one replaceable component—and by updating the software of the imaging arrangement.

BRIEF DESCRIPTION OP FIGURES

Figure 2:
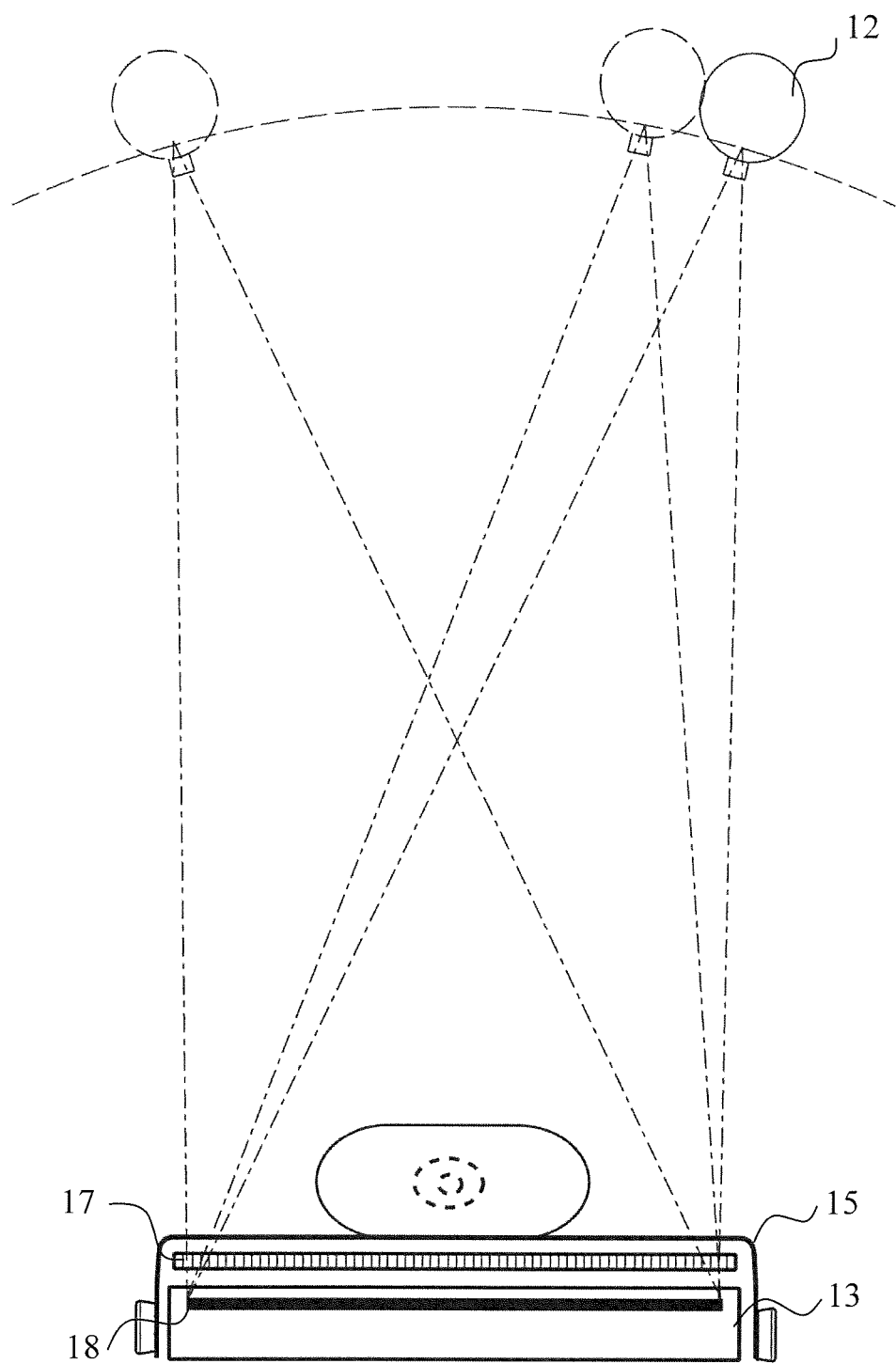
Figure 3:
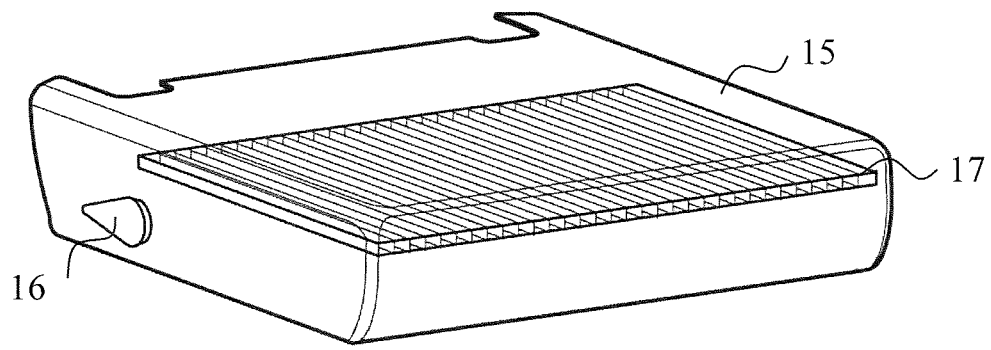
Figure 4:
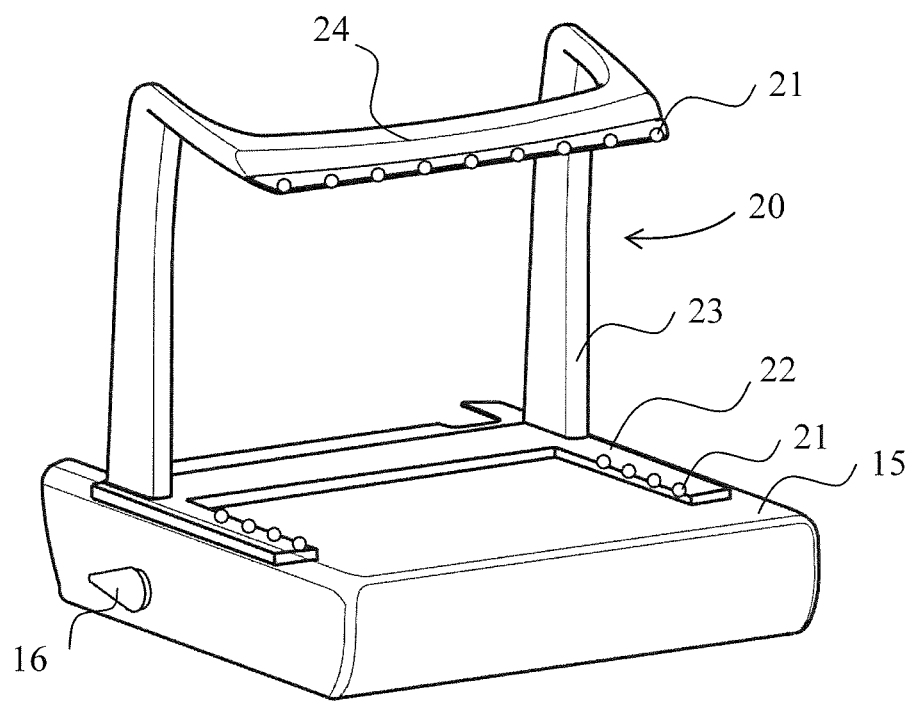
Figure 5:
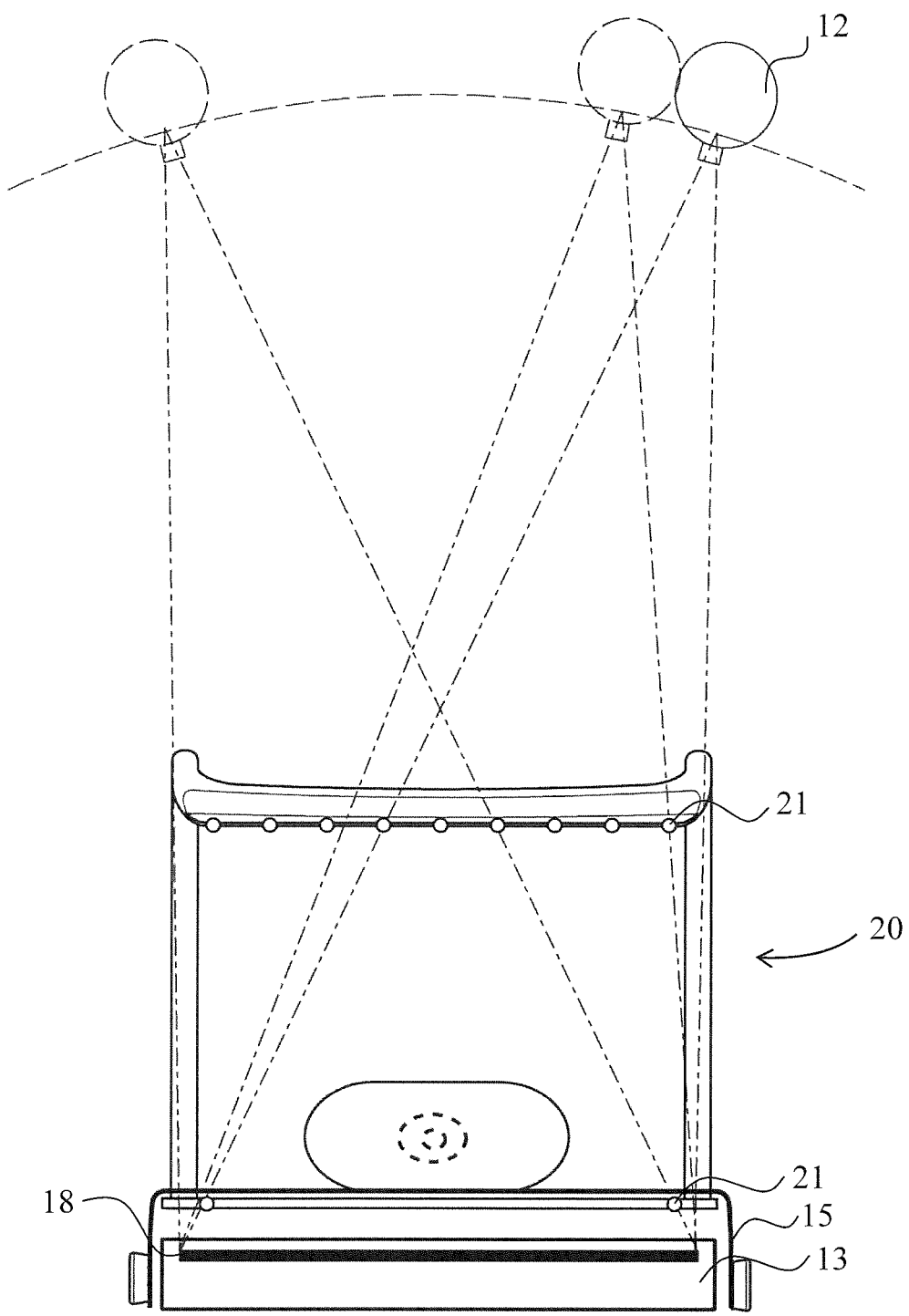
Figure 6A:
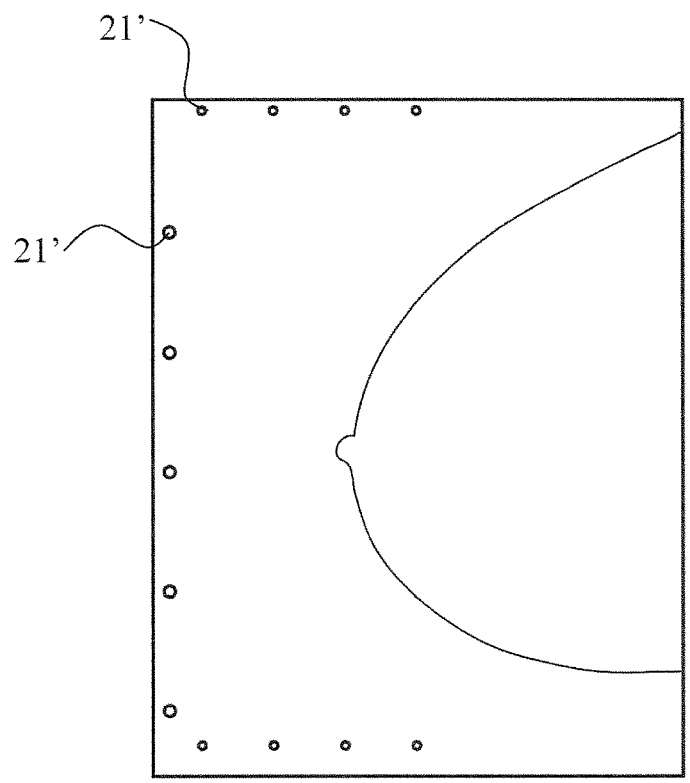
Figure 6B:
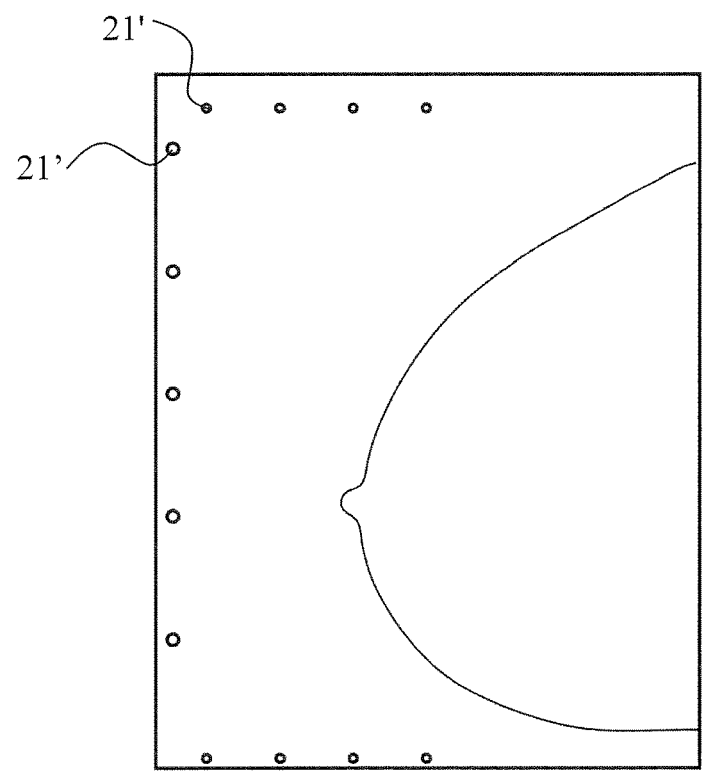
Figure 7:
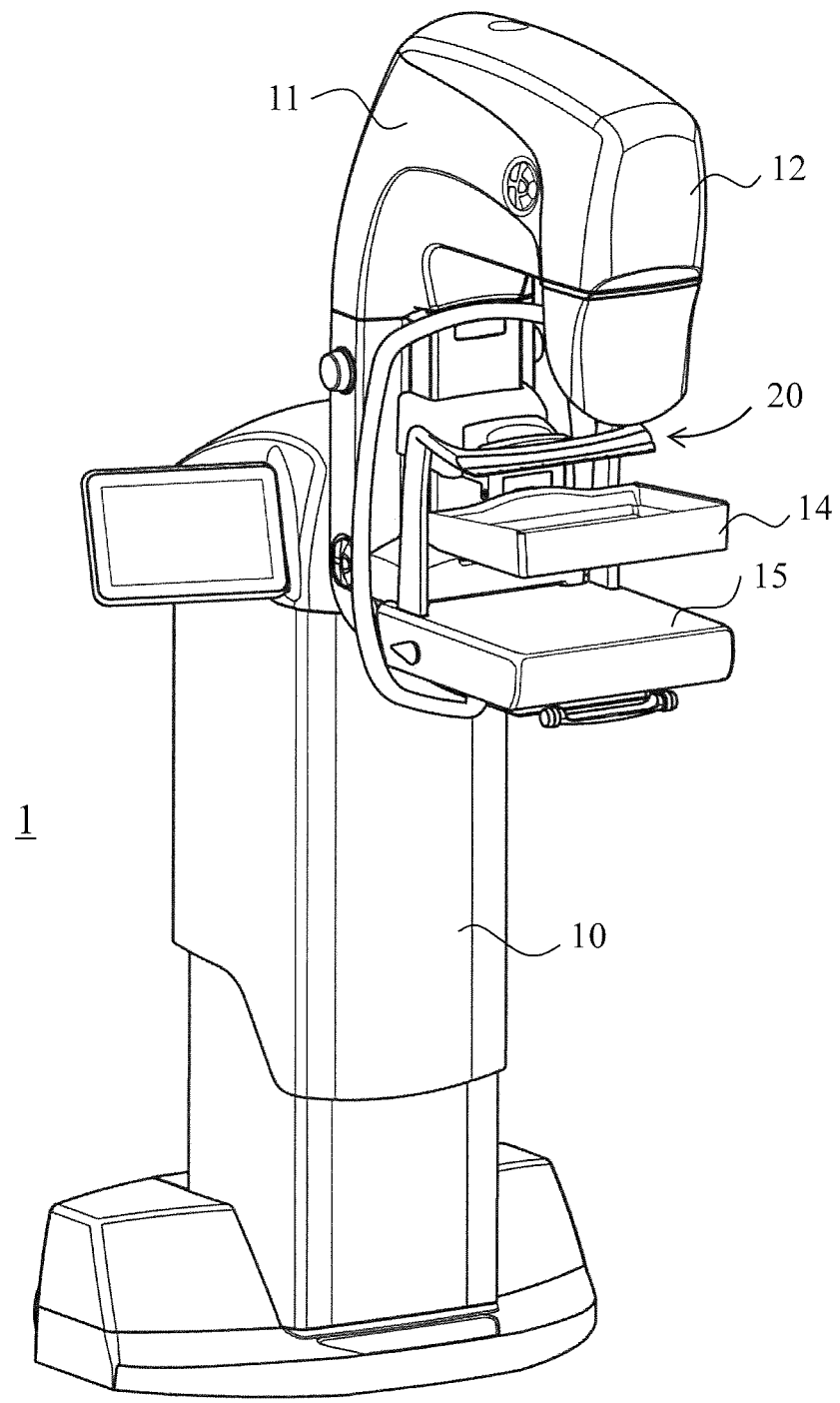
Figure 8:
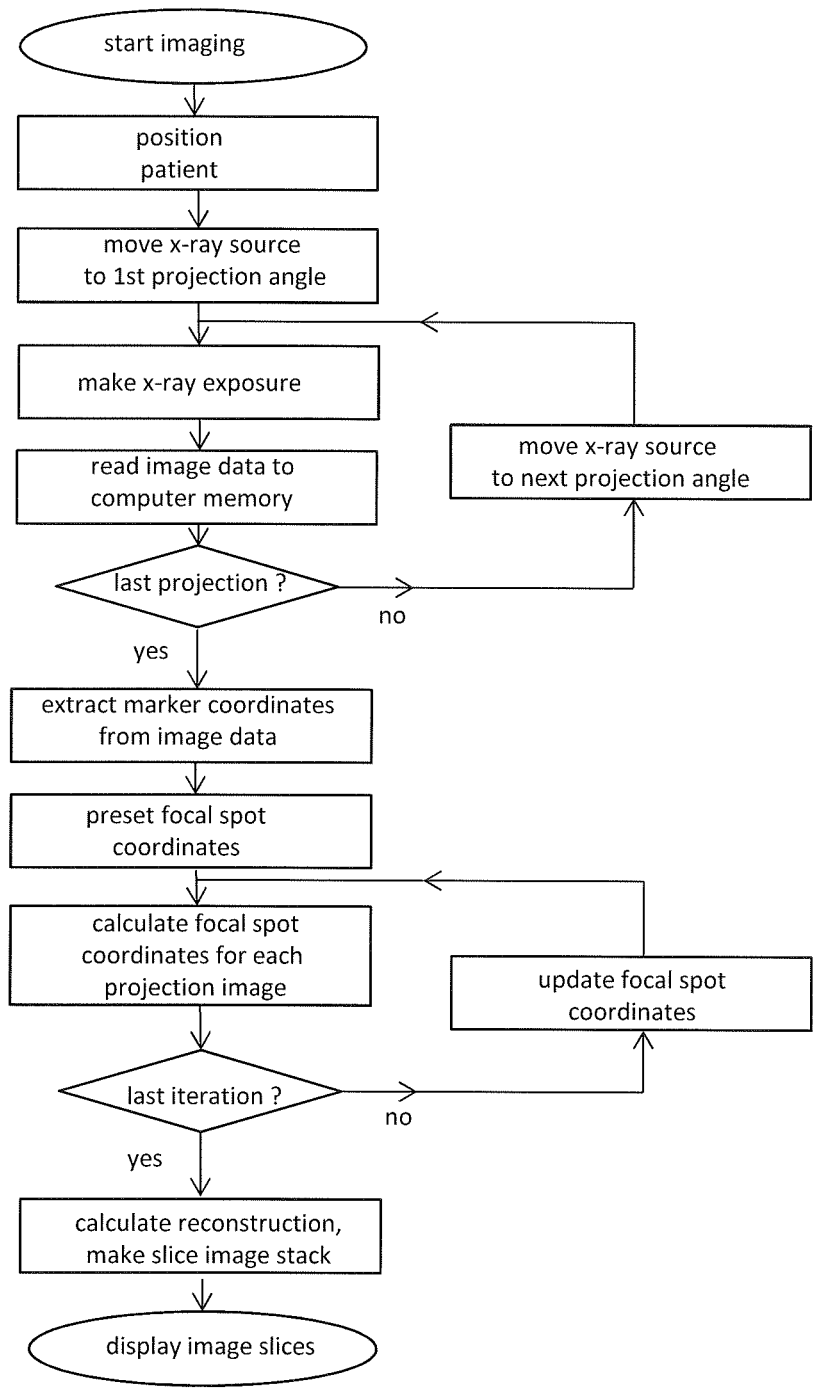
Figure 9:
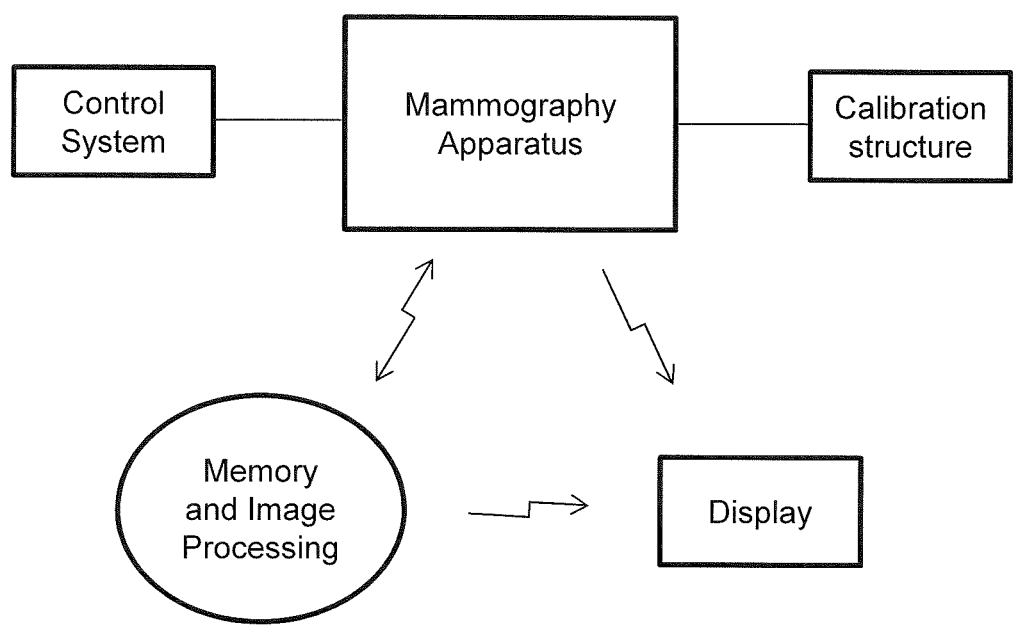

In the following, sane embodiments of the invention and their benefits will be described in more detail, also with help of the attached figures, of which figures FIG. 1 represents basic constructions of a typical mammography apparatus, FIG. 2 represents the principle of tomosynthesis, FIG. 3 represents one typical lower tray structure used in connection with a mammography apparatus, FIG. 4 represents one lower tray structure of a mammography apparatus applicable for use in connection with the invention, whereto is integrated one calibration structure according to the invention, FIGS. 5, 6a and 6b represent how calibration balls belonging to the lower tray structure according to FIG. 4 become imaged at different projection angles, FIG. 7 represents a mammography apparatus according to FIG. 1, whereto is attached a lower tray structure according to FIG. 4, FIG. 8 represents an operation principle of one imaging process according to the invention, and FIG. 9 is a diagrammatic representation of basic comments of one arrangement according to the invention.

DETAILED DESCRIPTION OF INVENTION

FIGS. 1-3 show typical constructions of a mammography apparatus. The mammography apparatus (1) of FIG. 1 consists of a frame part (10) and a C-arm (11) (more commonly an arm structure (11)) attached to it. In the top part of the C-arm (11) inside its coven is arranged a source of radiation (12) which is arranged to generate a beam, which passes through an upper compression plate (14) of the mammography apparatus (when such an upper compression plate is attached to the apparatus) and towards a detector (18) positioned in a detector housing (13). The detector housing (13) or a corresponding structure is typically arranged inside a lower tray structure (15), into connection with which lower tray structure (15) can be integrated a grid structure (17) which absorbs radiation scattering from the object being imaged. The lower tray structure (15) can be a fixed structure in the apparatus or it can be arranged detachably connected. As the top surface of the lower tray structure (15) typically operates as a platform onto which the breast is positioned for imaging, this structure is also often called a lower compression plate. In the solution according to FIG. 1, the lower tray structure (15) is arranged with connecting means (16) to enable detachable connecting of the lower tray structure (15) to the mammography apparatus (1).

A typical mammography apparatus of today is applicable for use in the arrangement according to the invention. Such apparatus is motorized so that the C-arm (11) is arranged movable in the vertical direction and rotatable around an axis which is typically a physical horizontal axis connecting the C-arm (11) to the frame part (10) of the apparatus. The C-arm (11) can be implemented in two parts, whereby the basic construction of the apparatus can include either a substantially vertically standing frame part (10) or a frame part (10) which can be fixed to a wall or a ceiling and an arm structure (11) in connection with it, arranged turnable relative to a horizontal rotation axis, out of the opposite ends of which arm structure (11) substantially at a first end is placed a radiation source (12) comprising a focus point and at a second and an an image data receiving means (18). The arm structure (11) can be implemented such that it enables independent turning of the first and and/or the second end of the arm structure (11) relative to the horizontal rotation axis. The arrangement can further include control means, which include an information recording means and a means for processing information related to the imaging, especially for processing image information.

FIG. 2 shows a principle of a typical tomosynthesis imaging in which individual images of a breast are taken at different projection angles, e.g. at an angle of about ±15 degrees from the vertical. Of image information thus acquired, it is possible to synthesize various tomographic images by means of applicable image processing software. FIG. 2 shows an arrangement in which only the position of the radiation source (12) with respect to the breast being imaged is deflected, but such arrangements are also known in which the C-arm (11) is turned as a whole such that the breast is held positioned at its place but the detector (18) follows the movement of the radiation source (12) on the opposite side of the breast being imaged.

As referred to above, the radiation source (12) can be arranged to move continuously from the starting position of the imaging procedure to its end position and, during this movement, the radiation source (12) to be switchable on for several abort irradiation periods to generate an X-radiation pulse. Another possibility is to move the radiation source (12) in stages such that, for each exposure, the movement of the C-arm (11) is stopped at a predetermined angular position. Still, a problem of the first of these arrangements is the inaccuracy of imaging caused by, inter alia, the movement of the radiation source during an exposure and, of the latter, the long duration of the imaging process caused by stopping the C-arm at a number of different imaging positions. Accordingly, an alternative solution has been developed in which the breast is always turned during short irradiation periods synchronically along the movement of the radiation source (12) such that it follows the movement of the radiation source, i.e. it remains stationary in the beam generated by the radiation source (12). In such an arrangement, during the time periods between the irradiation pulses, the breast can still be turned back in the opposite direction, if desired, e.g. back to the position at which it was prior to the previous irradiation pulse. Such back-and-forth turning movement of the breast can be arranged to be e.g. of less than one degree whereby it is so small that, in practice, the patient does not necessarily even notice it.

The grid structure (17) shown below the lower tray structure (15) in FIGS. 2 and 3 is typically used when taking conventional mammography images but in an imaging process in which the incidence angle of the beam and the grid structure (17) would significantly change at different projections, such a structure is not necessarily used. The operation principles of the grid structure (17) include arranging each of the lamellas oriented substantially towards the focus of the radiation source and it rust be possible to move this structure within the imaging area during an exposure such that it will not be projected at any particular point in the image taken of the breast. If the orientation of the lamellas is not arranged adjustable, the dimensions of the imaging arrangement may make using the grid structure (17) impossible in en imaging according to FIG. 2. Such a situation is created when the angle at which the radiation meets the grid structure becomes so large that the quanta having penetrated the breast are not able to travel through the lamella gaps to the detector any more but will be absorbed in the grid structure.

FIG. 4 shows one lower tray structure (15) of a mammography apparatus suitable for use in the invention. Such a structure can include the grid structure (17) shown in FIG. 3 or it can have been left out, but it is essential that the structure is arranged with reference balls (21) or other small objects absorbing X-radiation. In the solution according to FIG. 4, these balls (21) are integrated in various places in a calibration structure (20) comprising a wing-like support structure (24) attached to the lower tray structure (15). The calibration structure (20) shown in FIG. 4 comprises substantially on the two opposite edges of the lower tray structure (15) two base parts (22) which extend horizontally in parallel with the surface of the lower tray structure (15) and of which at least one, but in FIG. 4 both, comprise balls (21) and of which both base parts (22) branches off a substantially vertically extending supporting arm (23). These supporting arms (23) support between them a support structure (24) which also comprises said balls (21) or other small objects absorbing X-radiation.

In the solution according to FIG. 4, 4 pieces of balls (21) are arranged in both base parts (22) and 9 pieces in the support structure (24). In a preferable embodiment of the invention, the balls (21) or other small objects are particularly arranged onto at least two different planes, that is as a three-dimensional structure such that there are at least five of them and, thus, at least one of them is on a different plane than the others. One preferable solution according to the invention is to arrange to the calibration structure (20) according to FIG. 4, or to a corresponding structure, 6-8 pieces of balls (21) or other small objects substantially on the same plane close to the plane of the surface of the detector (18), preferably divided evenly or so evenly as possible with respect to the detector surface on the opposite edges of said plane and, on the other hand, 8-12 balls (21) or other small objects at a greater distance from the plane of the surface of the detector (18) than the abovementioned balls (21) or other small objects arranged close to the surface of the detector (18).

In the solution according to FIG. 4, balls (21) are integrated in connection with a corresponding lower tray structure (15) which is used in conventional mammography imaging (FIG. 3). This arrangement makes transfer from conventional mammography imaging to tomosynthesis imaging, and vice versa, easy just by replacing an appropriate lower tray structure (15) to the imaging apparatus. It is nevertheless possible to arrange the balls (21) in the mammography apparatus in sane other way than by means of the structure (20) shown in FIG. 4, too. Such a calibration structure (20) can be of moms other shape and it can be attached or be attachable to even some other place in the mammography apparatus than the lower tray structure (15). It is also possible to arrange balls (21) only on one plane.

For example, in the solution according to FIG. 4, balls (21) are positioned on a plane which is located above the top surface of the lower tray structure (15). On the other hand in FIG. 5, which illustrates how the balls (21) get projected at different imaging projections, i.e. at different positions of the beam generated by the radiation source (12), the balls (21) are positioned below the top surface of the lower tray structure (15), to its substantial proximity but nevertheless such that they are not attached to the surface of the lower tray structure (15). This positioning of the balls (21) aims at ensuring that e.g. the possible bending of the top surface of the lower tray structure (15), in the use situation, will not affect the location of the balls with (20) respect to the detector (18).

Considering positioning of the reference balls (21) in the imaging arrangement, it is preferable to arrange them at such a spot or spots at which they probably will not become projected on top of a breast positioned in the imaging apparatus in connection with an imaging event. Thus e.g. in the structure according to FIG. 4, the balls (21) are not arranged into proximity of that side of the lower tray structure (15) from the direction of which the patient is positioned in the imaging apparatus but to the sides adjacent to it. On the one hand, the distance from the detector (18) of the wing-like support structure (24) of the calibration structure (20) to which the balls (21) are attached to and, on the other hand, its extent from the back edge of the detector (18) to above it are implemented such that the balls (21) are imaged substantially onto the opposite edge of the image than the edge from the direction of which the patient is positioned to the imaging apparatus. FIGS. 6a and 6b show how the projections (21') of the reference balls (21) become imaged at the extreme positions of the radiation source (12) shown in FIG. 5.

The arrangement presented above describes a solution in which the radiation source (12) moves over a particular tomographic angle from one side of the vertical position of the arm structure (11) to its other side. One preferable embodiment of the invention nevertheless comprises a solution in which the movement of the arm structure (11) is implemented by always starting from such a position of the arm structure that its movement can be implemented, in its entirety, away from the patient positioned for imaging. This solution provides, inter alia, such an advantage that it is possible to avoid a possible startling and hence moving caused by the movement of the arm structure (11) towards the patient, which can result even in failure of the whole imaging.

FIG. 7 shows a mammography apparatus according to FIG. 1, whereto is attached a lower tray structure (15) comprising the calibration structure (20) according to FIG. 4. A tomosynthesis imaging process can proceed with such an imaging apparatus arrangement e.g. according to what is shown in FIG. 8. The process starts by positioning the patient for imaging, which in connection with the arrangement above means placing a breast on top of the lower tray structure (15) and possibly compressing it to be immovable by the upper compression plate (14). If the arm structure (11) of the apparatus, or the part of the arm structure comprising the radiation source (12), has not already been driven to the first projection angle of the imaging process, it will be driven there, after which the arrangement is ready for the first exposure. Image information detected by the detector (18) in connection with the exposure is read to record and the imaging is repeated at small projection angle intervals, e.g. at projection angle intervals of 2 degrees. After the imaging phase, location of projections (21') of the balls (21) is identified in each recorded image and an iteration process is executed related to each image in which starting from predetermined initial values, the coordinate point of the focus of the radiation source (12) is determined which corresponds to the location of the balls (21) projected on the image. This process relating to the image information of each individual exposure can also be implemented already during the actual imaging process, always as the new exposure ends. In the actual reconstruction of the image information the possible coordinates of the focus points of the radiation source (12) having deviated from the default value in this projection-specific imaging geometry determination process are then taken into account, after which process the tomographic image or images are ready to be displayed.

FIG. 9 is a diagrammatic representation of basic components of one arrangement according to the invention. The arrangement comprises a mammography imaging apparatus comprising a control system, to which apparatus can be attached a calibration structure comprising balls or other small objects absorbing X-radiation. Information on the mutual geometry of these balls or other small objects is recorded in a memory, which information together with information obtained from the projection images produced by the mammography apparatus are used in the tomosynthesis calculation process for forming and displaying tomographic images.

In the above preferable embodiment of the invention, the reference balls (21) are arranged to form a three-dimensional mutual geometry. This arrangement enables determining not only the location of the focus of the radiation source (12) with respect to the location of the detector (18) (e.g. location of its center) at the moment of taking an image but also the orientation of the detector (18), irrespective of how during the imaging process the apparatus structures have perhaps bent or moved as deviated from the calculatory default values.

The location of the focus point can also be determined in principle based on ball geometry arranged only on one plane, if one is willing not to consider e.g. such a possibility that the lower tray structure (15), onto which the balls (21) are attached, can bend during the imaging process. In other words, if one assumes that, referring to the above arrangement, the detector (18), its housing (13), the lower tray structure (15) and the calibration structure (20) supporting the balls (21) form a rigid piece, and no changes occur in the respective position of its parts during the imaging process, it is possible to determine the location of the focus point at the moment of taking each image also as based on the projections of the ball geometry arranged on one plane. Then, the balls (21) are preferably arranged on a plane which is located at a distance, such as preferably at the distance of at least 5 cm, from the detector (18).

One preferable way to control the mammography apparatus during the imaging process comprises the procedure already referred to in the above in which the radiation source (12) moves at a constant speed and in which the breast is always set to follow the movement of the radiation source (12) during short irradiation pulses. Due to such a synchronized movement, it is possible to avoid movement artefacts which will inevitably be created due to mutual movement of the radiation source (12) and the breast during exposures. Such an arrangement also enables using slightly longer exposure pulses and as a consequence, an apparatus used for conventional mammography imaging can also be used for tomographic imaging without the need to adopt a more powerful and thus heavier X-ray source than the kind used in conventional mammography apparatuses. On the other hand, as compared to the solutions in which the radiation source (12) is always halted for the duration of each individual exposure, by this arrangement the total time required for the imaging process becomes significantly shorter.

When an imaging process of the above kind is implemented such that the duration of irradiation pulses is always considerably shorter than the time between the pulses, whereby the distance the radiation source 12 moves during a pulse is short as compared with the distance it moves during the time between the pulses, if one so wishes there will always be plenty of time in the process to turn the breast back to its original orientation prior to the next irradiation pulse. One preferable way to implement such a solution is to always mechanically connect the lower part of the arm structure (11) (which comprises means (14, 15) for positioning the breast immovable) to the upper part of the arm structure (11) (which comprises the radiation source (12)) for the duration of the irradiation pulses, whereby it automatically turns along the movement of the upper part of the arm structure (11) at the same angular velocity and, at the time between the pulses, to drive the lower part of the arm structure (11) back to the position at which it was before the start of the previous pulse.

The invention and its preferable embodiments thus include a mammography imaging arrangement for tomosynthesis, which arrangement includes a mammography imaging apparatus (1) which includes a substantially vertically standing frame part (10) or a frame part (10) which can be fixed to a wall or a ceiling, an arm structure (11) in connection with said frame part (10) which is turnable relative to a horizontal rotation axis, wherein out of the opposite ends of said arm structure (11) substantially at the first end is placed an X-radiation source (12) comprising a focus point and substantially at the second end an image data receiving means (18). In connection with said second end of the arm structure (11) is additionally arranged a lower tray structure (15) which positions substantially on top of the image data receiving means (18). The arrangement also includes control means for moving at least one component of the arm structure (11) and for controlling operation of the image data receiving means (18) as well as processing means which include an information recording means and a means for processing information.

Attached to the mammography imaging apparatus (1) is one or more calibration structure components (20) including balls (21) or other small objects which absorb X-radiation, and this calibration structure component (20) and its attachment to the apparatus CO is implemented such that, in tomosynthesis imaging projections of the apparatus, said balls (21) or other small objects or at least a portion of them position in the apparatus into a volume which is covered by a radiation beam extending from the focus of the radiation source (12) to the Image data receiving means (18). Information on the mutual geometry of these balls (21) or other small objects is recorded in the processing means of the arrangement.

In such an arrangement, the balls (21) or other email objects can be arranged to position in the radiation beam such that they or at least a portion of them will be projected substantially on one or more edges of the image data receiving means (18) but excluding that edge from the direction of which an object to be imaged positions in the mammography apparatus for imaging. The calibration structure belonging to the arrangement can be attached to e.g. that end of the arm structure (11) whereto said lower tray structure (15) is arranged or directly to the lower tray structure (15).

The mutual geometry of the balls (21) or other small objects can be implemented as a three-dimensional structure e.g. such that they are arranged on at least two different planes, one of those planes being substantially close to the tap surface of the lower tray structure (15) and another plane a distance further from the top surface of the lower tray structure (15), above it. On the plane substantially close to the lower tray structure (15), it is preferable to place the balls (21) or other small objects at the proximity of one or two edges of the lower tray structure (15) which are side edges to that edge from the direction of which an object to be imaged is placed for imaging in the mammography apparatus, and on said plane a distance further from the top surface of said lower tray structure (15), above it at the proximity of but at a distance from an edge of the lower tray structure (15) opposite to that edge from the direction of which an object to be imaged is placed for imaging in the mammography apparatus.

The control system of the mammography apparatus can be arranged to control the radiation source (12) and the movements of the are structure (11) such that, within a certain angle range of movement of the arm structure (11), the radiation source (12) generates a radiation beam several times, the beam being directed towards said image data receiving means (18) such that also said balls (21) or other small objects or at least a portion of them are projected to each of the images, and said processing means be arranged to include means for determining, based an projections (21') of said balls (21) or other small objects, a coordinate point at which the focus of the radiation source (12) relative to the image data receiving means (18) was located upon taking the given image. When the balls (21) or other small objects are arranged in a three-dimensional geometry, the processing means of the apparatus can be arranged to comprise means to determine, based on the positions of projections (21') of said balls (21) or other small objects in each image, a distance between the focus of the radiation source (12) and a center of an active surface of the image data receiving means (18) as well as the orientation of a plane defined by the active surface of the image data receiving means (18) relative to a line passing through said focus of the radiation source (12) and the center of the active surface of the image data receiving means (18).

In one embodiment of the arrangement, the arm structure (11) is implemented in a way that enables turning of the first end of the arm structure (11), the second and of the arm structure (11) or both of them independently relative to a horizontal rotational axis. The arm structure (11) can also be implemented such that it enables the turning of the first end of the arm structure (11) comprising the radiation source (12) into different tomosynthesis imaging projections such that the second end of the arm structure (11) comprising the image data receiving means (18) does not follow the movement of the first end of the arm structure (11) but remains stationary.

Furthermore, the structure of the mammography apparatus may be implemented such that to said arm structure (11), above said lower tray structure (15), is arranged an upper compression plate (14) which is arranged movable along the arm structure (11) and said lower tray structure (15) and upper compression plate (14) are arranged turnable relative to the arm structure (11), that said control system is arranged to turn the arm structure (11) supporting the radiation source (12) at a substantially uniform angular velocity and, during this movement, to control the radiation source (12) to generate radiation pulses, and said lower tray structure (15) and upper compression plate (14) are arranged to turn during these radiation pulses at the same angular velocity and in the same direction as by which the arm structure (11) moves the radiation source (12) and, during the time periods between said radiation pulses, to remain stationary or to move at a different angular velocity or to move in a different direction than the radiation source (12).

The one or more calibration structures (20) belonging to the arrangement including balls (21) or other small objects can be realized as attached to said lower tray structure (15) and the lower tray structure (15) arranged as detachably attached to the mammography imaging apparatus (1). Hereby, the arrangement can include a first lower tray structure (15) arranged as detachably attachable and including one or more calibration structures (20) for said balls (21) or other small objects, and a second lower tray structure (15) arranged as detachably attachable and whereto is arranged a radiation absorbing grid structure (17).

When a lower tray structure (15) is used in the arrangement wherein balls (21) or other small objects are arranged to one or more calibration structures (20) on at least two different planes, such a calibration structure (20) can be arranged to comprise at substantially at least two edges of the lower tray structure (15) a base part (22) extending horizontally as parallel with the surface of the lower tray structure (15), at least one of the base parts (22) including balls (21) or other small objects, and out of at least one of these base parts (22) branches off a substantially vertically extending support arm (23) which supports a support structure (24) which also includes X-radiation absorbing balls (21) or other small objects. For example in this kind of arrangement, it is possible to arrange the balls (21) or other small objects below the surface of the lower tray structure (15) to its immediate proximity.

Embodiments of invention can also be considered including a mammography imaging method which utilizes a mammography imaging apparatus (1) including an arm structure (11) arranged turnable relative to a rotation axis and supporting a radiation source (12), in which method, a breast is positioned to the apparatus for imaging and the radiation source (12) is moved along a curved trajectory over a given angle range, during which movement, a radiation beam is generated several times at the radiation source (12), which beam is directed towards the breast positioned in the apparatus and image data receiving means (16). In the method, one or more calibration structures (20) including X-radiation absorbing balls (21) or other small objects in a known mutual geometry are attached to a mammography apparatus and the calibration structure (20) and its attachment to the apparatus (1) are implemented such that the balls (21) or other small objects or at least a portion of them will get placed, within said angle range of movement of the radiation source, into a volume which is covered by the radiation beam extending from a focus of the radiation source (12) to the image data receiving means (18). Now, the balls (21) or other small objects or at least a portion of them are projected to each image taken in the method, whereby concerning each of the images, a coordinate point can be determined based on the locations of projections (21') of said balls (21) or other small objects at which the focus of the radiation source (12) relative to the image data receiving means (18) was located upon taking the given image. A tomographic image or a series of layers of the breast being imaged can then be reconstructed by using in the calculation for each image knowledge of location of the focus of radiation source (12) as determined according to this method.

When balls (21) or other small objects are placed in a calibration structure component (20) in a known mutual three-dimensional geometry, it is possible to determine, based on the positions of their projections (21') in each image, a distance between the focus of the radiation source (12) and a center of an active surface of the image data receiving means (18) as well as the orientation of a plane defined by the active surface of the image data receiving means (18) relative to a line passing through said focus of the radiation source and the center of the active surface of the image data receiving means (18).

The invention claimed is:

1. A lower tray structure which is to be attached to or attached in connection with an arm structure supporting a radiation source and an image data receiving means of a mammography imaging apparatus, characterized in that the lower tray structure includes at least one calibration structure component including X-radiation absorbing balls or other small objects arranged to at least two different planes, wherein said at least one calibration structure component includes on substantially at least two edges of the lower tray structure a base part extending horizontally as parallel with the surface of the lower tray structure, at least one of the base parts including said balls or other small objects, and out of these base parts from at least one branches off a substantially vertically extending support arm which supports a support structure which also includes said X-radiation absorbing balls or other small objects.

2. The lower tray structure according to claim 1, characterized in that a portion of said balls or other small objects is arranged below a surface of the lower tray structure, to its immediate proximity.

3. The lower tray structure of claim 1, wherein at least several of said X-radiation absorbing balls or other small objects are located proximate an edge of the lower tray structure.

4. A mammography imaging method in which a mammography imaging apparatus is used, said imaging apparatus including an arm structure arranged turnable relative to a rotation axis and supporting a radiation source and in which out of the opposite ends of said arm structure, substantially at the first end, is placed an x-radiation source comprising a focus point and substantially at the second end an image data receiving means and wherein in connection with said second end of the arm structure is further arranged a lower tray structure which positions substantially on top of the image data receiving means, in which method a breast is positioned to the apparatus for imaging and the radiation source is moved along a curved trajectory over a given angular range, during which movement, a radiation beam is generated several times at the radiation source, which beam is directed towards the image data receiving means and the breast positioned in the apparatus, characterized in that at least one calibration structure component is provided, said calibration structure component including X-radiation absorbing balls or other small objects arranged to at least two different planes, wherein said at least one calibration structure component includes on substantially at least two edges of the lower tray structure a base part extending horizontally as parallel with the surface of the lower tray structure, at least one of the base parts including said balls or other small objects, and out of these base parts from at least one branches off a substantially vertically extending support arm which supports a support structure which also includes said X-radiation absorbing balls or other small objects, wherein the X-radiation absorbing balls or other small objects are placed in a known mutual three-dimensional geometry, said calibration structure component having a fixed spacing from the radiation source which remains the same fixed spacing during positioning of a patient, compressing of the breast, and imaging of the breast, and the at least one or more calibration structure component and attachment thereof to the apparatus are implemented such that said balls or other small objects or at least a portion of them will get placed within said angular range of movement of the radiation source into a volume which the radiation beam extending from a focus of the radiation source to the image data receiving means covers, whereby said balls or other small objects or at least a portion of them are projected to images taken in the method and wherein that coordinate point at which the focus of the radiation source relative to the image data receiving means was located upon taking the given image is determined as based on the locations of projections of said balls or other small objects, and in which a single tomographic image or a series of layers of the breast being imaged is reconstructed by using in the calculation, the knowledge thus determined of location of the focus of the radiation source when taking an individual image.

5. The method according to claim 4, characterized in that based on positions of projections of said balls or other small objects in each image, a distance between the focus of the radiation source and a center of an active surface of the image data receiving means is determined, as well as an orientation of a plane defined by the active surface of the image data receiving means relative to a line passing through said focus of the radiation source and the center of the active surface of the image data receiving means.

\* \* \* \* \*